United States Patent
Racheboeuf

(10) Patent No.: US 9,949,964 B2
(45) Date of Patent: Apr. 24, 2018

(54) TESOFENSINE COMPOSITIONS

(71) Applicant: Saniona A/S, Ballerup (DK)

(72) Inventor: Bruno Racheboeuf, Reims (FR)

(73) Assignee: Saniona A/S, Baltorpvej (DK)

( * ) Notice: Subject to any disclaimer, the term of this patent is extended or adjusted under 35 U.S.C. 154(b) by 0 days.

(21) Appl. No.: 15/698,115

(22) Filed: Sep. 7, 2017

(65) Prior Publication Data

US 2018/0064700 A1    Mar. 8, 2018

(30) Foreign Application Priority Data

Sep. 7, 2016   (EP) ..................................... 16187596
Sep. 8, 2016   (EP) ..................................... 16187813

(51) Int. Cl.
*A61K 31/46*   (2006.01)
*A61K 9/28*    (2006.01)
*A61K 9/20*    (2006.01)

(52) U.S. Cl.
CPC ............ *A61K 31/46* (2013.01); *A61K 9/2013* (2013.01); *A61K 9/2018* (2013.01); *A61K 9/2054* (2013.01); *A61K 9/2095* (2013.01); *A61K 9/28* (2013.01); *A61K 9/2813* (2013.01); *A61K 9/2853* (2013.01); *A61K 9/2866* (2013.01); *A61K 9/2893* (2013.01)

(58) Field of Classification Search
None
See application file for complete search history.

(56) References Cited

U.S. PATENT DOCUMENTS

| | | | | |
|---|---|---|---|---|
| 4,140,756 A | * | 2/1979 | Gallian ................ | A61K 9/2013 424/475 |
| 4,654,206 A | * | 3/1987 | Okuda ................... | A61K 9/146 424/480 |
| 5,977,158 A | * | 11/1999 | Rasmussen .......... | A61K 9/2018 514/422 |
| 8,202,884 B2 | | 6/2012 | Dugi et al. | |
| 2001/0022972 A1 | * | 9/2001 | Chittamuru .......... | A61K 9/2813 424/439 |
| 2003/0198670 A1 | * | 10/2003 | Kumbhani ........... | A61K 9/2054 424/468 |
| 2012/0115837 A1 | | 5/2012 | Hoshina et al. | |

FOREIGN PATENT DOCUMENTS

| | | | | |
|---|---|---|---|---|
| WO | WO 97/30997 | * | 8/1997 | ............. A61K 31/46 |
| WO | WO 2005/073228 | | 8/2005 | |
| WO | WO 2009/080691 A2 | | 7/2009 | |
| WO | WO 2011/039337 A1 | | 4/2011 | |
| WO | WO 2013/120935 | | 8/2013 | |

OTHER PUBLICATIONS

Astrup et al., "Effect of tesofensine on bodyweight loss, body composition, and quality of life in obese patients: a randomised, double-blind, placebo-controlled trial", The Lancet, Nov. 29, 2008, vol. 372, 1906-1913.
International Patent Application No. PCT/EP2017/072462: International Search Report dated Dec. 15, 2017, 14 pages.
Wharton et al., "Next Generation of Weight Management Medications: Implications for Diabetes and CVD Risk", Current Cardiology Reports, May 2015, 17:35, 9 pages.

* cited by examiner

*Primary Examiner* — Aradhana Sasan
(74) *Attorney, Agent, or Firm* — Baker & Hostetler LLP

(57) ABSTRACT

The present invention relates to tesofensine compositions, methods to prepare the same and uses thereof in preparing medicines for the prevention and treatment of overweight, obesity and type 2 diabetes mellitus.

27 Claims, 2 Drawing Sheets

TESOFENSINE COMPOSITIONS

CROSS REFERENCE TO RELATED APPLICATION

This application claims the benefit of EP Application No. 16187596.8, filed Sep. 7, 2016, and EP Application No. 16187813.7, filed Sep. 8, 2016, the entireties of which are incorporated by reference herein.

FIELD OF THE INVENTION

The present invention relates to tesofensine compositions, methods to prepare the same and uses thereof in preparing medicines for the prevention and treatment of overweight, obesity and type 2 diabetes mellitus.

BACKGROUND OF THE INVENTION

The prevalence of overweight and obesity and associated comorbidities in the human population has increased at an unprecedented rate in recent years. The United Nations has estimated that if this trend continues, 17% of adults globally will be obese by 2025. That is, there will be 170 million adults with a BMI >35. If the estimate also adds overweight population, there will be 2.7 billion overweight adults by 2025, well above the 2 billion of 2010.

Type 2 diabetes mellitus is one the greatest impact comorbidities associated with overweight and obesity. It has been estimated that the number of adults with diabetes has almost quadrupled from 108 million adults who had diabetes in the year 1980 to 422 million adults in 2014. Diabetic complications can lead to heart attacks, blindness, renal failure or limb amputation, among other consequences. It is believed that 43% of premature deaths (before age 70) occurring due to diabetes are preventable by the adoption of policies supporting a healthy life style, as well as through improved methods of detection and treatment of the illness.

Consequently, there is a global commitment to prevent, detect and treat overweight and obesity, and associated comorbidities, since these diseases have profound physical, psychological and socioeconomic impacts.

The active ingredient tesofensine, (3S,4R)-3-(3,4-dichlorphenyl)-4-(ethoxymethyl)-8-methyl-8-azabicyclo[3.2.1]octane, first described in WO 97/30997, is a monoamine reuptake inhibitor. WO 97/30997 suggests that tesofensine may be used to treat obesity. It has been taught that tesofensine has the potential to produce weight loss at a better rate than currently approved drugs. It has also been found that tesofensine has the potential to reverse the progress of type 2 diabetes mellitus by decreasing hepatic fat, and also has beneficial effects on plasma insulin concentration and glycated hemoglobin (HbAlc) (U.S. Pat. No. 8,202,884 B2; Astrup A, Madsbad S, Breum L, Jensen T, Kroustrup J and Meinert T (2008) *Lancet* 372(9653): 1906-13; Wharton S and Serodio K (2015) *Curr Cardiol Rep.* 17(5):35). WO 2005/073228 describes isolation, purification and large scale production of tesofensine.

Preclinical and clinical studies conducted with tesofensine have increased the knowledge on the drug's mechanism of action and have generated new findings regarding its use for treating conditions of overweight, obesity and type 2 diabetes mellitus.

The prior art has also taught the doses at which tesofensine would provide the desired therapeutic effects, and has disclosed compositions of tesofensine in combination with other active ingredients such as metoprolol (WO 2013/120935).

One skilled in the art would know that establishing the stability of a pharmaceutical composition is a determining factor since the chemical stability of pharmaceutical molecules can affect the safety and efficacy of a medicament. Testing the stability of a pharmaceutical product is essential to understand how the quality of the drug and that of the final product changes over time under several environmental conditions. Applicants are required to observe this prerequisite to obtain a marketing authorization.

Evaluation of the drug's stability is critical to achieve safe and effective formulations and pharmaceutical forms, as well as to select proper packaging. On the other hand, the dissolution profile is a key indicator of the quality and is inherently related with the selection of the proper excipients as well as with the selection of the manufacture equipment and best preparation methods.

In view of the potential of tesofensine in medicine, it would be advantageous to have qualitative and quantitative formulations of tesofensine. It would also be advantageous if such pharmaceutical formulations were sufficiently stable and effective so that they can be used commercially to prepare medicaments indicated for the prevention and treatment of overweight, obesity and type 2 diabetes mellitus. Specifically, it would be advantageous to identify pharmaceutical compositions showing bioavailability and chemical stability, and a low content of impurities. It is also desirable to obtain orally administerable, commercial, pharmaceutical tesofensine compositions, without compromising bioavailability or stability.

SUMMARY OF THE INVENTION

The present invention relates to pharmaceutical compositions which comprise tesofensine as active ingredient, pharmaceutically acceptable salts or derivatives thereof, and their use for preparing medicaments indicated for the prevention and treatment of overweight, obesity and type 2 diabetes mellitus.

Qualitative and quantitative pharmaceutical compositions of tesofensine with the desired release profile and optimal chemical stability are herein provided. Such pharmaceutical compositions may be used for preparing orally administered medicaments indicated for the prevention and treatment of overweight, obesity and type 2 diabetes mellitus.

In a first embodiment the present disclosure relates to stable pharmaceutical compositions of tesofensine comprising therapeutically effective amounts of tesofensine, or pharmaceutically acceptable salts or derivatives thereof, intimately mixed with pharmaceutically acceptable excipients, formulated as an oral dosage form, and methods to prepare the same.

A stable pharmaceutical composition herein disclosed and formulated to be administered orally comprises a coated tablet comprising:
  a) a tablet core comprising tesofensine intimately mixed with pharmaceutically acceptable excipients; and
  b) a coating film;
    wherein the coated tablet comprises 0.30% to 0.70% by weight of tesofensine.

Preferably, the pharmaceutically acceptable excipients in the tablet core consist of or consist essentially of hydroxypropylcellulose, lactose monohydrate, croscarmellose sodium, microcrystalline cellulose, magnesium stearate, or a combination thereof, and optionally a solvent. By carefully selecting these excipients and avoiding povidones and polyethylene glycol in the tablet core, very stable tablets can be obtained. Experiments have unexpectedly demonstrated that formulating tesofensine with povidone and PEG results in degradation of Tesofensine over time.

The tablets may comprise 0.25 mg to 1.0 mg tesofensine, measured as the free base.

The tesofensine may constitute from 0.30% to 0.70% by weight of the total weight of the composition, the pharmaceutically acceptable excipients may constitute from 96% to 98% by weight of the total weight of the composition, and the filmcoat may constitute from 2% to 3% by weight of the total weight of the composition.

Examples of pharmaceutically acceptable excipients for use in the tablets of the disclosure include one or more from the group consisting of fillers, binders, disintegrants, lubricants and solvents.

The filmcoat of the disclosed tablets may comprise one or more from the group consisting of coating agents, plasticizers, solvents, glidants and pigments.

The tesofensine used herein can be the free base or a tesofensine salt, preferably, tesofensine citrate.

In another embodiment, the disclosure relates to stable pharmaceutical compositions of tesofensine comprising therapeutically effective amounts of tesofensine, or pharmaceutically acceptable salts or derivatives thereof, intimately mixed with pharmaceutically acceptable excipients, useful for preparing medicaments indicated for the prevention and treatment of overweight, obesity and type 2 diabetes mellitus.

DETAILED DESCRIPTION OF THE INVENTION

Figure 1:
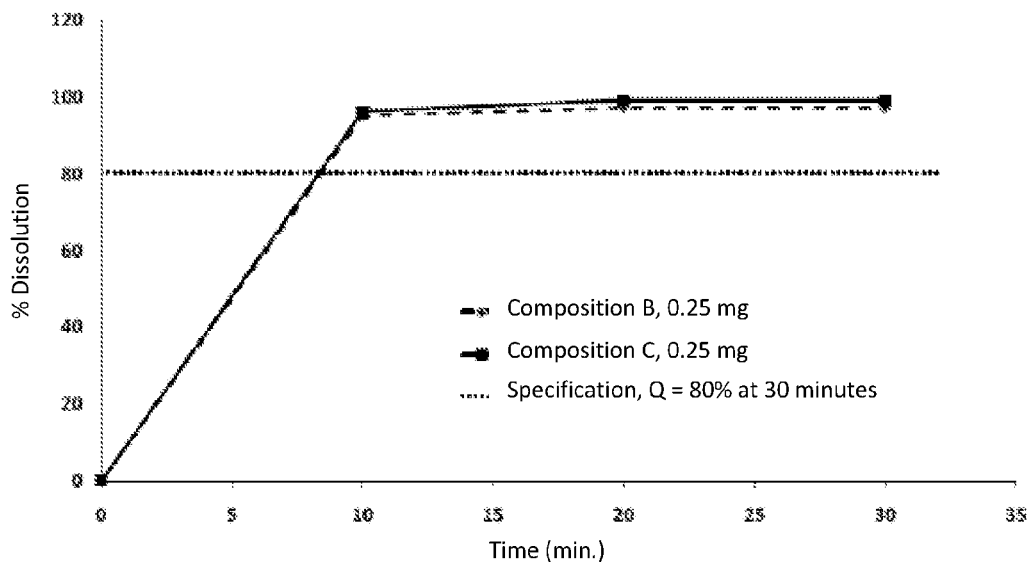
FIG. 1 is a chart showing the dissolution profile of two pharmaceutical compositions of tesofensine formulated as coated tablets with a dose-strength of 0.25 mg.

The technical terms of the present specification and claim set are used with the meaning commonly understood by one skilled in the art unless otherwise stated.

As used herein, the term "active ingredient" refers to the substances having a therapeutic effect. Specifically, the active ingredient is tesofensine, also including pharmaceutically acceptable and active salts, derivatives and forms thereof. It will be understood that the terms "drug" and "active substance" are synonyms of "active ingredient".

The term "pharmaceutically acceptable" is used herein to refer to a material which is safe for oral administration and which has the desired function or activity without having undesirable toxic or biological effects nor prejudicial interactions with any of the ingredients of the composition.

The term "pharmaceutically active" as used herein refers to a material which has the desired pharmacological effect.

The term "effective amount" as used herein indicates that the ingredient is present in an amount which is not toxic and which is effective to produce the desired effect.

As used herein, the term "therapeutically effective amount" indicates that the active ingredient in the composition is present in an amount which is not toxic and which is effective to produce the desired pharmacological effect. It will be understood that the "therapeutically effective amount" of the active ingredient refers to the amount of the active ingredient as free base, and not to the amount of salts or derivatives of the active ingredient added to the composition.

The term "dose strength" is used herein to refer to the amount of active ingredient measured in units of concentration. It will be understood that the term "dose strength" refers to the amount of the active ingredient as free base and not to the amount of salts or derivatives of the active ingredient which are added to the composition.

The term "excipient" is used herein to refer to a pharmacologically inactive substance which serves as the medium to incorporate one or more active ingredients during the manufacture of a product. It will be understood that the term "excipient" includes the term "vehicle".

The term "tesofensine", as used herein refers to the compound represented by Formula I of systemic name (3S,4R)-3-(3,4-dichlorophenyl)-4-(ethoxymethyl)-8-methyl-8-azabicyclo[3.2.1]octane], and molecular formula $C_{17}H_{23}Cl_2NO$. It will be understood that the term "tesofensine" includes the specified chemical entity, as well as pharmaceutically acceptable salts, derivatives or forms thereof.

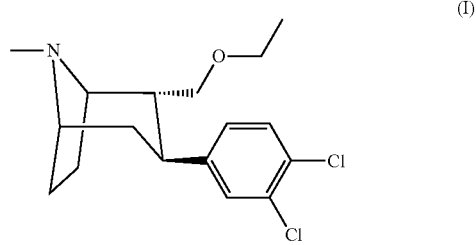 [SMILES: CCOC[C@H]1C2CCC(C[C@@H]1c1ccc(Cl)c(Cl)c1)N2C]

(I)

The term "salts" is used herein to refer to the salts of the compound of Formula I which are safe and effective for oral administration and have pharmacological activity, including but not limited to, acid addition salts and base addition salts.

The term "tesofensine citrate" or "tesofensine citrate salt" or "citrate of tesofensine" as used herein refers to the compound represented by Formula II of systemic name (1 S,3 S,4R,5R)-3-(3,4-dichlorophenyl)-4-(ethoxymethyl)-8-methyl-8-azabicyclo[3.2.1]octane; 2-hydroxypropane-1,2,3-tricarboxylic acid), and molecular formula $C_{23}H_{31}Cl_2NO_8$.

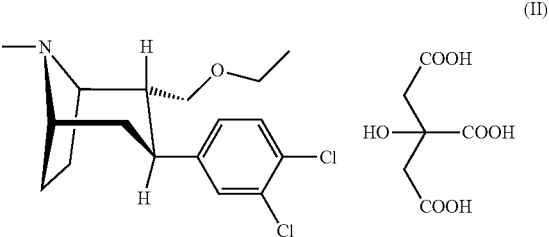

(II)

The term "stable" as used herein refers to a pharmaceutical composition which maintains a pharmaceutically acceptable condition during an extended period, e.g. at least six months, preferably one year, such as two years and more preferably at least three years, during which the composition is stored at room temperature and low humidity.

The term "binder" as used herein is a pharmaceutically acceptable excipient that has the property of holding the tablet together after pressing the tablet. A binder gives the tablet its required mechanical strength and also contributes to its volume ("filler") as it is usually present in significant amounts.

The term "filler" or "bulking agent" as used herein is a pharmaceutically acceptable excipient that contributes to the volume of the tablet. Fillers are often used to give volume to pharmaceutically potent drugs, so that the tablet achieves a certain size and can be handled by the patients. Some tablet components may serve as both a "filler" and a "binder".

The term "disintegrant" as used herein is a pharmaceutically acceptable excipient that serves to expand and dissolve the tablet when wet causing the tablet to break apart in the digestive tract.

The term "lubricant" as used herein is a pharmaceutically acceptable excipient that serves to prevent ingredients from clumping together and from sticking to surfaces during the mixing and tableting process.

Drug Excipient Compatibility

A compatibility study investigating the chemical stability of binary mixtures of tesofensine and pharmaceutically acceptable excipients has been conducted. Incompatibility was observed for the following excipients: povidone, crospovidone, copovidone, macrogol 400, macrogol 6000, magnesium stearate, titanium dioxide and possibly colloidal silicon dioxide.

For the povidones and macrogols, an unexpected oxidative degradation to N-oxides was observed. The povidones should be avoided in commercial tesofensine solid dosage forms.

For the macrogols, the most extensive decomposition was observed for macrogol 400. As macrogols are often used as plasticizers in film coatings, a limited contact with the drug substance is expected. However, it is recommended to use macrogol 6000 as plasticizer since significant decomposition was observed only at a storage temperature of 60° C., whereas an unexpected and considerable extent of decomposition was observed with macrogol 400.

Incompatibility with colloidal silica was also unexpectedly observed, but it was also found that its presence may not be relevant in a pharmaceutical composition of tesofensine.

Regarding magnesium stearate, the extent of decomposition was low irrespective of the storage condition, and the low content of this excipient in an oral dose formulation, such as a tablet, may be considered acceptable. Long-term and accelerated stability studies with oral formulations comprising magnesium stearate confirmed that this excipient at low levels does not initiate any significant decomposition.

Titanium dioxide was found to provoke extensive decomposition under very dry conditions (40° C. and approx. 0% relative humidity). Therefore, this excipient is only used in small quantities as white pigment in a film coat, which limits the contact with the drug substance, which also was supported by long term and accelerated stability studies.

Pharmaceutical Compositions

Oral administration of the pharmaceutical compositions is preferred. A composition comprises a therapeutic effective amount of the active ingredient for oral administration, wherein oral administration is adapted to have the form of any of the following: tablet, soft gel capsule, hard gel capsule, dispersible powder, granule, suspension, elixir, dispersion liquid, or any pharmaceutical form reasonably adapted for oral administration. In one embodiment capsules and tablets are preferred as oral administration forms, more preferably film-coated tablets.

Immediate release compositions are preferred since the in-vivo half-life of the active ingredient is in the range of days.

Having established the compatibility of excipients, in a preferred embodiment pharmaceutically acceptable excipients are selected for preparing a stable tesofensine composition. Non-limiting examples of commercially available and pharmaceutically acceptable excipients suitable for preparing the stable tesofensine composition are described below.

In a preferred embodiment, lactose monohydrate was selected as the primary filler as lactose has superior compression characteristics and was compatible with the active ingredient. Microcrystalline cellulose was selected as filler in the final blend as microcrystalline cellulose was superior to lactose monohydrate with respect to tablet hardness and tablet hardness variation. Microcrystalline cellulose also was compatible with the active ingredient. Hydroxypropylcellulose was selected as binder due to its compatibility with the active ingredient. The amount of binder was adequate to provide sufficient resistance to crushing and plasticity of the granules. Crosscarmelllose sodium was selected as disintegrant as it is an effective disintegrant and is compatible with the active ingredient. The amount of croscarmellose sodium was sufficient to provide the desired disintegration. The amount of magnesium stearate selected was sufficient to avoid sticking to tableting tooling during compression. Ethanol was selected as co-solvent in the granulating liquid as ethanol evaporates easily for improved drying properties of the granulate. The solubility of the active ingredient was also increased in ethanol/mixtures compared to pure water or ethanol.

Thus in a preferred embodiment, a dried tablet core comprises or consists of Tesofensine, lactose monohydrate, microcrystalline cellulose, hydroxypropylcellulose, croscarmellose sodium, and magnesium stearate and optionally any non-evaporated water and ethanol.

For the coating, Macrogol 6000 was selected as plasticizer. Compatibility studies had proven macrogols to be incompatible with the active ingredient, however it was shown that the incompatibility was dependent of the polymer chain length. The shorter the chain length the less compatible the macrogol was with the active ingredient. As macrogol 6000 is present only in the coating suspension and the content is low, it is concluded that Macrogol 6000 could be used as plasticizer. Likewise, titanium dioxide was applied as pigment even though it proved to be incompatible with the active ingredient. Iron oxide was selected as it provided the desired final color of the coated tablets.

According to one embodiment, pharmaceutical formulations of tesofensine are developed as coated tablets with different dose strengths based in the selection of pharmaceutically acceptable excipients.

In one embodiment, the pharmaceutically acceptable excipients are hydroxypropylcellulose, lactose monohydrate, croscarmellose sodium, microcrystalline cellulose, and magnesium stearate. More preferably, the tablet core consists of or consists essentially of tesofensine, hydroxypropylcellulose, lactose monohydrate, croscarmellose sodium, microcrystalline cellulose, and magnesium stearate. Optionally, the tablet core may comprise any residual solvent such as water or alcohol, which has not evaporated.

The core part of the dried tablet may thus comprise:
a) 90-98 weight % binder and filler, such as 93-97%, such as 95-96%;
b) 1-3 weight % disintegrant, such as 1.5-2.5%;
c) 0.5-1.5 weight % lubricant, such as 0.75-1%; and
d) 0.5-1.5 weight % binder, such as 0.75-1.25%.

The core part of the dried tablet may comprise:
a) 40-80 weight % filler, such as 50-80%, such as 60-70%, such as 66-67%;
b) 20-60 weight % filler/binder, such as 40-60 weight %, such as 25-35%;
c) 1-3 weight % disintegrant, such as 1.5-2.5%;
d) 0.5-1.5 weight % lubricant, such as 0.75-1%; and
e) 0.5-1.5 weight % binder, such as 0.75-1.25%.

Preferably the pharmaceutically acceptable excipients used for the tablet core are hydroxypropylcellulose, lactose monohydrate, croscarmellose sodium, microcrystalline cellulose, and magnesium stearate. These excipients provide a combination of stability to the active ingredient and to the tablet.

The tablet core may consist of or may consist essentially of tesofensine, hydroxypropylcellulose, lactose monohydrate, croscarmellose sodium, microcrystalline cellulose, and magnesium stearate.

In embodiments of the present disclosure the core part of the dried tablet comprises
a) 90-98 weight % lactose, e.g. lactose monohydrate, and cellulose, such as microcrystalline cellulose such as 93-97%, such as 95-96%;
b) 1-3 weight % crosscarmellose sodium, such as 1.5-2.5%;
c) 0.5-1.5 weight % magnesium stearate, such as 0.75-1%; and
d) 0.5-1.5 weight % hydroxypropylcellulose, such as 0.75-1.25%.

In other embodiments, the core part of the dried tablet comprises or consists of:
a) 40-80 weight % lactose, e.g. lactose monohydrate, such as 40-70%, such as 50-80%, such as 60-70%, such as 66-67%;
b) 20-50 weight % microcrystalline cellulose, such as 20-40% such as 25-35%;
c) 1-3 weight % crosscarmellose sodium, such as 1.5-2.5%;
d) 0.5-1.5 weight % magnesium stearate, such as 0.75-1%; and
e) 0.5-1.5 weight % hydroxypropylcellulose, such as 0.75-1.25%; and
f) tesofensine, or a pharmaceutically acceptable salt thereof.

In embodiments, the tablet core consists of:
a) 40-80 weight % lactose, e.g. lactose monohydrate, such as 40-70%, such as 50-80%, such as 60-70%, such as 66-67%;
b) 20-50 weight % microcrystalline cellulose, such as 20-40% such as 25-35%;
c) 1-3 weight % crosscarmellose sodium, such as 1.5-2.5%;
d) 0.5-1.5 weight % magnesium stearate, such as 0.75-1%; and
e) 0.5-1.5 weight % hydroxypropylcellulose, such as 0.75-1.25%; and
f) tesofensine, or a pharmaceutically acceptable salt thereof.

The coating film may be made from hypromellose, titanium dioxide, macrogol 6,000, talcum, and iron oxide, or it may be a commercially available coating film, such as Opadry or others.

In another embodiment, the coating film consists essentially of hypromellose, titanium dioxide, macrogol 6,000, talcum, and iron oxide. Optionally, the film may comprise any residual solvent such as water or alcohol, which has not evaporated.

Due to the mentioned drug incompatibilities, the tablet core preferably does not comprise povidone (polyvinylpyrolidone, PVP), crospovidone (polyvinylpolypyrolidone, PVPP), copovidone (polyvinylpyrolidone vinylacetate copolymer), macrogol (polyethyleneglycol, PEG), and titanium dioxide. Still further, the tablet core may not comprise colloidal silicon dioxide.

Tesofensine suitably is tesofensine citrate.

In some embodiments tesofensine is the only active ingredient in the pharmaceutical compositions. For example, in other embodiments, the pharmaceutical compositions do not comprise any beta-blocker.

In a preferred embodiment, the pharmaceutical compositions of tesofensine are formulated as coated tablets with a dose-strength of 0.25 mg, 0.5 mg and 1.0 mg. Methods to prepare the pharmaceutical compositions are described below.

The coated tablets may be stored in typical blister packages, such as PVC/PVCD-aluminum blisters, and in plastic bottles such as HDPE bottles for extended storage.

Method to Prepare Coated Tablets

The excipients used for preparing the pharmaceutical compositions are commercially available. Synthesis of the active ingredient, Tesofensine, follows the teachings of WO 2005/073228.

Pharmaceutical compositions herein disclosed can be prepared by traditional and acceptable pharmaceutical techniques. In a preferred embodiment the pharmaceutical compositions of tesofensine are formulated as coated tablets.

In one embodiment the coated tablets are prepared as follows: the active ingredient and hydroxypropylcellulose is dissolved in a water/ethanol mixture (granulation liquid). In a high-shear mixer lactose monohydrate is premixed using the impeller. The lactose blend is wetted with the granulation liquid mixture by spraying under constant operation of the impeller. Drying of granulate is performed using a fluid bed dryer. The granulate is sieved. Croscarmellose sodium and microcrystalline cellulose is sieved and premixed with the intermediate granulated product. Magnesium stearate is sieved and added to the premixed blend. The final blend is tableted using a rotatory tablet press. Coating of tablets is performed by spraying the coating suspension onto the tablet cores in a rotating coating pan, forming the film-coated tablets.

Accordingly there is provided a process to prepare the composition according to any of the preceding claims, wherein the process comprises de steps of:
a) forming a tablet core which comprises tesofensine and pharmaceutically acceptable excipients, wherein the tesofensine constitutes from 0.40% to 0.70% by weight of the total weight of the composition, the pharmaceutically acceptable excipients constitute from 96% to 97% by weight of the total weight of the composition; and
b) forming a film-coated tablet by spraying the filmcoat onto the tablet core, wherein the filmcoat constitutes from 2% to 3% by weight of the total weight of the composition.

Preferably the method comprises forming a tablet core by:
a) dissolving tesofensine and hydroxypropylcellulose in a granulation liquid to obtain a granulation liquid mixture;
b) wetting lactose monohydrate with the granulation liquid mixture;
c) drying and sieving the wetted granulate;
d) mixing the granulate with croscarmellose sodium, microcrystalline cellulose, and magnesium stearate; and
e) tableting the final blend into tablet cores.

The film coat may comprise or consist essentially of hypromellose, macrogol 6000, titanium dioxide, talcum, and iron oxide.

The tesofensine may be tesofensine citrate.

In some embodiments tesofensine is the only active ingredient in the tablet. In other embodiments, the tablet does not comprise any beta-blocker.

Clinical Uses

The pharmaceutical compositions disclosed herein can be used for preparing medicaments indicated for preventing and treating of one or more of the conditions selected from the group consisting of: overweight, obesity and one or more associated comorbidities.

In a preferred embodiment the compositions are used for preparing medicaments indicated for preventing and treating one or more of the conditions selected from the group consisting of: overweight, obesity and one or more associated comorbidities, wherein the one or more associated comorbidities are selected from the group consisting of type 2 diabetes mellitus, obesity hypoventilation syndrome, obstructive sleep apnea syndrome, hypertension, cardiovascular disease, some types of neoplasia, degenerative joint disease, dyslipidemia, gastroesophageal reflux disease, choleliathesis, fatty liver, infertility, polycystic ovarian syndrome, urinary incontinence, nephrolithiasis, some types of cancer, venous insufficiency, atrial fibrillation, congestive heart failure, and benign intracranial hypertension. More preferably the compositions are used in the preparation of medicaments indicated for preventing and treating one or more of the conditions selected from the group consisting of: overweight, obesity and one or more associated comorbidities, wherein the one or more associated comorbidity is type 2 diabetes mellitus.

The compositions can be administered through any appropriate form capable of contacting the drug with the drug action site in a subject.

The pharmaceutical compositions are useful for preparing medicaments indicated for preventing and treating overweight, obesity and type 2 diabetes mellitus. The daily dose will depend on factors such as the subject's requirements and the condition to be treated. The daily dose of the compositions herein described may be administered to a subject in need of said compositions as a single dose or as multiple doses.

In one embodiment the preferred oral administration forms are discrete units each containing a therapeutically effective amount of active ingredient, such as tablets or capsules. In a preferred embodiment, there is provided a pharmaceutical composition of tesofensine formulated as coated tablets.

In another preferred embodiment, the pharmaceutical compositions of tesofensine useful in the preparation of medicaments used to prevent and treat overweight, obesity and type 2 diabetes mellitus, comprise tesofensine in a therapeutically effective amount. More preferably the pharmaceutical compositions of tesofensine useful for preparing medicaments used to prevent and treat overweight, obesity and type 2 diabetes mellitus, comprise tesofensine in an amount ranging from 0.40% to 0.70% w/w.

In a preferred embodiment, the pharmaceutical compositions of tesofensine useful for preparing medicaments used to prevent and treat overweight, obesity and type 2 diabetes mellitus, comprise tesofensine as tesofensine citrate in an amount ranging from 0.40% to 0.70% w/w.

In one embodiment, the pharmaceutical compositions of tesofensine useful in the preparation of medicaments used to prevent and treat overweight, obesity and type 2 diabetes mellitus, have a dose strength ranging from 0.25 mg to 1.0 mg. Preferably, the pharmaceutical compositions of tesofensine useful for preparing medicaments used to prevent and treat overweight, obesity and type 2 diabetes mellitus, have a dose strength of 0.25 mg, 0.5 mg, or 1.0 mg.

Numbered Items

The invention is in the following described as numbered items:

1. A stable pharmaceutical composition formulated to be orally administrable, characterized in that the pharmaceutical composition comprises a coated tablet comprising:
   a) a tablet core comprising tesofensine intimately mixed with pharmaceutically acceptable excipients; and
   b) a coating film;
   wherein the coated tablet comprises from 0.30% to 0.70% by weight of tesofensine.
2. The pharmaceutical composition according to item 1, wherein the tesofensine constitutes from 0.30% to 0.70% by weight of the total weight of the composition, the pharmaceutically acceptable excipients constitute from 96% to 98% by weight of the total weight of the composition, and the filmcoat constitutes from 2% to 3% by weight of the total weight of the composition.
3. The pharmaceutical composition according to any of the preceding items, wherein the pharmaceutically acceptable excipients comprise one or more from the group consisting of filler, binders, disintegrants, lubricants and solvents.
4. The pharmaceutical composition according to item 3, wherein the filler is selected from lactose, such as lactose monohydrate, and cellulose, such as microcrystalline cellulose.
5. The pharmaceutical composition according to items 3, wherein the binder is selected from cellulose, such as microcrystalline cellulose, and hydroxypropylcellulose.
6. The pharmaceutical composition according to any of the items 3-5, wherein the disintegrant is crosscarmellose sodium.
7. The pharmaceutical composition according to any of the items 3-6, wherein the lubricant is magnesium stearate.
8. The pharmaceutical composition according to any of the items 3-7, wherein the solvent is selected from water and ethanol, preferably wherein the solvent has been evaporated to dryness.
9. The pharmaceutical composition according to any of the preceding items 3-8, wherein the core part of the dried tablet comprises
   a) 90-98 weight % binder and filler, such as 93-97%, such as 95-96%;
   b) 1-3 weight % disintegrant, such as 1.5-2.5%;
   c) 0.5-1.5 weight % lubricant, such as 0.75-1%; and
   d) 0.5-1.5 weight % binder, such as 0.75-1.25%.

10. The pharmaceutical composition according to any of the preceding items 3-9, wherein the core part of the dried tablet comprises
a) 40-80 weight % filler, such as 50-80%, such as 60-70%, such as 66-67%;
b) 20-60 weight % filler/binder, such as 40-60 weight %, such as 25-35%;
c) 1-3 weight % disintegrant, such as 1.5-2.5%;
d) 0.5-1.5 weight % lubricant, such as 0.75-1%; and
e) 0.5-1.5 weight % binder, such as 0.75-1.25%.

11. The pharmaceutical composition according to any of the preceding items, wherein the pharmaceutically acceptable excipients are hydroxypropylcellulose, lactose monohydrate, croscarmellose sodium, microcrystalline cellulose, and magnesium stearate.

12. The pharmaceutical composition according to any of the preceding items, wherein the tablet core consists of or consists essentially of tesofensine, hydroxypropylcellulose, lactose monohydrate, croscarmellose sodium, microcrystalline cellulose, and magnesium stearate.

13. The pharmaceutical composition according to any of the preceding items 3-10, wherein the core part of the dried tablet comprises
a) 90-98 weight % lactose, e.g. lactose monohydrate, and cellulose, such as microcrystalline cellulose such as 93-97%, such as 95-96%;
b) 1-3 weight % crosscarmellose sodium, such as 1.5-2.5%;
c) 0.5-1.5 weight % magnesium stearate, such as 0.75-1%; and
d) 0.5-1.5 weight % hydroxypropylcellulose, such as 0.75-1.25%.

14. The pharmaceutical composition according to any of the preceding items 3-11, wherein the core part of the dried tablet comprises
a) 40-80 weight % lactose, e.g. lactose monohydrate, such as 40-70%, such as 50-80%, such as 60-70%, such as 66-67%;
b) 20-50 weight % microcrystalline cellulose, such as 20-40% such as 25-35%;
c) 1-3 weight % crosscarmellose sodium, such as 1.5-2.5%;
d) 0.5-1.5 weight % magnesium stearate, such as 0.75-1%; and
e) 0.5-1.5 weight % hydroxypropylcellulose, such as 0.75-1.25%.

15. The pharmaceutical composition according to any of the preceding items 3-10, wherein the tablet core consists of:
a) 90-98 weight % lactose, e.g. lactose monohydrate, and cellulose, such as microcrystalline cellulose such as 93-97%, such as 95-96%;
b) 1-3 weight % crosscarmellose sodium, such as 1.5-2.5%;
c) 0.5-1.5 weight % magnesium stearate, such as 0.75-1%; and
d) 0.5-1.5 weight % hydroxypropylcellulose, such as 0.75-1.25%; and
e) tesofensine, or a pharmaceutically acceptable salt thereof.

16. The pharmaceutical composition according to any of the preceding items 3-11, wherein the tablet core consists of:
a) 40-80 weight % lactose, e.g. lactose monohydrate, such as 40-70%, such as 50-80%, such as 60-70%, such as 66-67%;
b) 20-50 weight % microcrystalline cellulose, such as 20-40% such as 25-35%;
c) 1-3 weight % crosscarmellose sodium, such as 1.5-2.5%;
d) 0.5-1.5 weight % magnesium stearate, such as 0.75-1%; and
e) 0.5-1.5 weight % hydroxypropylcellulose, such as 0.75-1.25%; and
f) tesofensine, or a pharmaceutically acceptable salt thereof.

17. The pharmaceutical composition according to any of the preceding items, wherein the filmcoat comprises one or more from the group consisting of coating agents, plasticizers, solvents, glidants and pigments.

18. The pharmaceutical composition according to item 17, wherein the coating agent is hypromellose.

19. The pharmaceutical composition according to item 17-18, wherein the plasticizer is macrogol, preferably a macrogol with a molecular weight above 2,000, such as macrogol 6,000.

20. The pharmaceutical composition according to any of items 17-19, wherein the glidant is talcum.

21. The pharmaceutical composition according to any of the items 17-20, wherein the pigment is selected from titanium oxide and iron oxide.

22. The pharmaceutical composition according to any of the items 17-21, wherein the solvent is selected from water and ethanol, preferably wherein the solvent has been evaporated to dryness.

23. The pharmaceutical composition according to any of the items 17-22, wherein the dried film coating comprises:
a. 30-70 weight % coating agent, such as 40-60%, such as 45-55%;
b. 2.5-10 weight % plasticizer, such as 3-8%, such as 4-6%;
c. 20-40 weight % pigment, such as 25-35%; and
d. 10-20% glidant, such as 12.5-17.5%.

24. The pharmaceutical composition according to any of the items 17-22, wherein the dried film coating comprises:
a. 30-70 weight % hypromellose, such as 40-60%, such as 45-55%;
b. 2.5-10 weight % macrogol 6,000, such as 3-8%, such as 4-6%;
c. 20-30 weight % titanium oxide;
d. 2.5-7.5 weight % iron oxide; and
e. 10-20% talcum, such as 12.5-17.5%.

25. The pharmaceutical composition according to any of the preceding items, wherein the coating film comprises hypromellose, titanium dioxide, macrogol 6,000, talcum, and iron oxide.

26. The pharmaceutical composition according to any of the preceding items, wherein the coating film consists essentially of hypromellose, titanium dioxide, macrogol 6,000, talcum, and iron oxide.

27. The pharmaceutical composition according to any of the preceding items, wherein the tablet core does not comprise povidone (polyvinylpyrolidone, PVP), crospovidone (polyvinylpolypyrolidone, PVPP), copovidone (polyvinylpyrolidone vinylacetate copolymer), macrogol (polyethyleneglycol, PEG), and titanium dioxide, optionally wherein the tablet core further does not comprise colloidal silicon dioxide.

28. The pharmaceutical composition according to any of the preceding items, wherein the tesofensine is tesofensine citrate.

29. The pharmaceutical composition according to any of the preceding items, wherein tesofensine is the only active ingredient.
30. The pharmaceutical composition according to any of the preceding items, which does not comprise any beta-blocker.
31. A process to prepare the composition according to any of the preceding items, wherein the process comprises de steps of:
   a) forming a tablet core which comprises tesofensine and pharmaceutically acceptable excipients, wherein the tesofensine constitutes from 0.30% to 0.70% by weight of the total weight of the composition, the pharmaceutically acceptable excipients constitute from 96% to 98% by weight of the total weight of the composition; and
   b) forming a film-coated tablet by spraying the filmcoat onto the tablet core, wherein the filmcoat constitutes from 2% to 3% by weight of the total weight of the composition.
32. The method of item 31, comprising forming a tablet core by:
   a) dissolving tesofensine and a binder in a granulation liquid to obtain a granulation liquid mixture;
   b) wetting a filler with the granulation liquid mixture;
   c) drying and sieving the wetted granulate;
   d) mixing the granulate with disintegrant, filler/binder, and lubricant; and
   e) tableting the final blend into tablet cores.
33. The method of any of the items 31 or 32, wherein the granulation liquid comprises water and ethanol.
34. The method of any of the items 31 to 33, wherein the film coat comprises hypromellose, macrogol 6000, titanium dioxide, talcum, and iron oxide.
35. The method of any of the items 31 to 34, wherein the tablet core comprises tesofensine, hydroxypropylcellulose, lactose monohydrate, croscarmellose sodium, microcrystalline cellulose, and magnesium stearate.
36. The method of any of the items 31 to 34, wherein the tablet core consists of tesofensine, hydroxypropylcellulose, lactose monohydrate, croscarmellose sodium, microcrystalline cellulose, and magnesium stearate.
37. The method of any of the items 31 to 35, wherein the tablet core does not comprise povidone (polyvinylpyrolidone, PVP), crospovidone (polyvinylpolypyrolidone, PVPP), copovidone (polyvinylpyrolidone vinylacetate copolymer), macrogol (polyethyleneglycol, PEG), and titanium dioxide, optionally wherein the tablet core further does not comprise colloidal silicon dioxide.
38. The method of any of the items 31 to 36, wherein the tesofensine is tesofensine citrate.
39. The method of any of the items 31 to 38, wherein tesofensine is the only active ingredient in the tablet.
40. The method of any of the items 31 to 39, wherein the tablet does not comprise any beta-blocker.
41. The use of the pharmaceutical composition according to any of the items 1-30 for preparing a medicament for preventing and treating overweight and obesity, and associated comorbidities.
42. The use according to item 41, wherein the associated comorbidity is type 2 diabetes mellitus.
43. The use according to item 41 or 42, wherein the medicament is adapted to supply a dose of 0.25 to 1.0 mg of tesofensine, measured as free base, per tablet.

The following examples illustrate aspects of the present disclosure but should not be construed as limitations. Examples 1, 2 and 3 teach novel stable compositions comprising tesofensine and pharmaceutically acceptable excipients, and methods to prepare said compositions.

EXAMPLE 1

Composition A

Tesofensine coated tablets with a dose strength of 0.25 mg, 0.5 mg and 1.0 mg were developed based on the selection of pharmaceutically acceptable excipients. The qualitative and quantitative formulation of the coated tablet is shown in table 1.

Given the low content of the active ingredient a granulation process, in which the active ingredient is dissolved in the granulation fluid, was developed to achieve adequate content uniformity of the tablets. The manufacturing method made use of a one-pot vacuum granulation in which granulation and drying was performed in the same equipment. Final blend for 0.25 mg coated tablets contains 0.44% of tesofensine. Final blend for 0.5 mg and 1.0 mg coated tablets contains 0.66% of tesofensine, which gives the opportunity to use the same manufacturing procedure for granulate despite the different tablet dose strengths. Differentiation into 0.5 mg or 1.0 mg is accomplished by tooling size and tablet mass during tablet compression. Compression was performed using a rotatory tablet press. Physical size of the tablets was used to differentiate among strengths. The tablets were coated with an aqueous solution/suspension containing iron dioxide and titanium dioxide in order to improve physiochemical stability. Tablet cores were coated using a pan coater.

TABLE 1

Qualitative and quantitative composition of tesofensine coated tablets. Composition A.

| | Composition | | | |
|---|---|---|---|---|
| | 0.25 mg | 0.5 mg | 1.0 mg | |
| Ingredient | mg/tablet | mg/tablet | mg/tablet | |
| | Tablet diameter | | | |
| | 6 mm | 7 mm | 9 mm | Function |
| Tablet core | | | | |
| Tesofensine# | 0.3963 | 0.7930 | 1.5850 | Active |
| Lactose monohydrate | 59.2290 | 78.7070 | 157.4150 | Filler |

TABLE 1-continued

Qualitative and quantitative composition of tesofensine coated tablets.
Composition A.

| Ingredient | Composition | | | Function |
|---|---|---|---|---|
| | 0.25 mg | 0.5 mg | 1.0 mg | |
| | mg/tablet | mg/tablet | mg/tablet | |
| | Tablet diameter | | | |
| | 6 mm | 7 mm | 9 mm | |
| Microcrystalline cellulose | 27.0000 | 36.0000 | 72.0000 | Filler/Binder |
| Hydroxypropylcellulose | 0.9000 | 1.2000 | 2.4000 | Binder |
| Croscarmellose sodium | 1.8000 | 2.4000 | 4.8000 | Disintegrant |
| Magnesium stearate | 0.6750 | 0.9000 | 1.8000 | Lubricant |
| Ethanol 96%* | (10.06) | (13.440) | (26.880) | Solvent |
| Purified water* | (6.71) | (8.960) | (17.920) | Solvent |
| Film coat | | | | |
| Hypromellose | 1.2500 | 1.5000 | 2.5000 | Coating agent |
| Macrogol 6000 | 0.1250 | 0.1500 | 0.2500 | Plasticizer |
| Titanium dioxide | 0.6240 | 0.7500 | 1.2500 | Pigment |
| Talcum | 0.3750 | 0.4500 | 0.7500 | Glidant |
| Iron oxide | 0.1250 | 0.1500 | 0.2500 | Pigment |
| Water* | (17.008) | (20.400) | (34.00) | Solvent |
| Total | 92.5 | 123.0 | 245.0 | |

Added as tesofensine citrate, and corresponds to a dose strength of 0.25 mg, 0.5 mg or 1.0 mg, respectively, of tesofensine free base. //
*Volatile components.

EXAMPLE 2

Composition B

Tesofensine coated tablets with a dose strength of 0.25 mg, 0.5 mg and 1.0 mg were developed based on the selection of pharmaceutically acceptable excipients. The qualitative and quantitative formulation of the coated tablet is shown in table 2.

Method of preparation of composition B was the same as that used to prepare composition A (example 1), with the difference that magnesium stearate was slightly increased due to adhesion to compression tooling. The manufacture procedure was also changes so that the intra-granular phase only consisted of lactose monohydrate as filler. The microcrystalline cellulose was solely added in the final blending phase. This procedure increased the resistance to crushing to the desired level and the amount of granulation was reduced accordingly.

TABLE 2

Qualitative and quantitative composition of tesofensine coated tablets. Composition B.

| Ingredient | Composition | | | Function |
|---|---|---|---|---|
| | 0.25 mg | 0.5 mg | 1.0 mg | |
| | mg/tablet | mg/tablet | mg/tablet | |
| | Tablet diameter | | | |
| | 6 mm | 7 mm | 9 mm | |
| Tablet core | | | | |
| Tesofensine# | 0.3963 | 0.7926 | 1.5822 | Active |
| Lactose monohydrate | 59.0037 | 78.4074 | 156.8148 | Filler |
| Microcrystalline cellulose | 27.0000 | 36.0000 | 72.0000 | Filler/Binder |
| Hydroxypropylcellulose | 0.9000 | 1.2000 | 2.4000 | Binder |
| Croscarmellose sodium | 1.8000 | 2.4000 | 4.8000 | Disintegrant |
| Magnesium stearate | 0.9000 | 1.2000 | 2.4000 | Lubricant |
| Ethanol 96%* | (5.2134) | (6.9512) | (13.9024) | Solvent |
| Water* | (3.4756) | (4.6341) | (9.2682) | Solvent |
| Film coat | | | | |
| Hypromellose | 1.2500 | 1.5000 | 2.5000 | Coating agent |
| Macrogol 6000 | 0.1250 | 0.1500 | 0.2500 | Plasticizer |
| Titanium dioxide | 0.6250 | 0.7500 | 1.2500 | Pigment |
| Talcum | 0.3750 | 0.4500 | 0.7500 | Glidant |

TABLE 2-continued

Qualitative and quantitative composition of tesofensine coated tablets. Composition B.

| Ingredient | Composition | | | Function |
|---|---|---|---|---|
| | 0.25 mg | 0.5 mg | 1.0 mg | |
| | mg/tablet | mg/tablet | mg/tablet | |
| | Tablet diameter | | | |
| | 6 mm | 7 mm | 9 mm | |
| Iron oxide | 0.1250 | 0.1500 | 0.2500 | Pigment |
| Purified water* | (18.7000) | (22.4400) | (37.4000) | Solvent |
| Total | 92.5 | 123.0 | 245.0 | |

Added as tesofensine citrate, and corresponds to a dose strength of 0.25 mg, 0.5 mg or 1.0 mg, respectively, of tesofensine free base. //
*Volatile components.

EXAMPLE 3

Composition C

Tesofensine coated tablets with a dose strength of 0.25 mg, 0.5 mg and 1.0 mg were developed based on the selection of pharmaceutically acceptable excipients. The qualitative and quantitative formulation of the coated tablet is shown in table 3.

The preparation method of compositions A and B was slightly modified to prepare composition C. The granulation was performed using a traditional high-shear mixer successively dried using a fluid bed dryer. Tableting was performed using a conventional equipment and coated with the film coat.

TABLE 3

Qualitative and quantitative composition of tesofensine coated tablets. Composition C.

| Ingredient | Composition | | | Function |
|---|---|---|---|---|
| | 0.25 mg | 0.5 mg | 1.0 mg | |
| | mg/tablet | mg/tablet | mg/tablet | |
| | Tablet diameter | | | |
| | 6 mm | 7 mm | 9 mm | |
| Tablet core | | | | |
| Tesofensine# | 0.3963 | 0.7926 | 1.5852 | Active |
| Lactose monohydrate | 59.0037 | 78.4074 | 156.8148 | Filler |
| Microcrystalline cellulose | 27.0000 | 36.0000 | 72.0000 | Filler/Binder |
| Hydroxypropylcellulose | 0.9000 | 1.2000 | 2.4000 | Binder |
| Croscarmellose sodium | 1.8000 | 2.4000 | 4.8000 | Disintegrant |
| Magnesium stearate | 0.9000 | 1.2000 | 2.4000 | Lubricant |
| Ethanol 96%* | (6.02)** | (7.29)** | (16.05)** | Solvent |
| Water* | (4.50) | (5.15) | (11.99) | Solvent |
| Film coat | | | | |
| Hypromellose | 1.2500 | 1.5000 | 2.5000 | Coating agent |
| Macrogol 6000 | 0.1250 | 0.1500 | 0.25000 | Plasticizer |
| Titanium dioxide | 0.5000 | 0.6000 | 1.0000 | Pigment |
| Talcum | 0.3750 | 0.4500 | 0.7500 | Glidant |
| Iron oxide | 0.2500 | 0.3000 | 0.5000 | Pigment |
| Water* | (17.5000) | (21.0000) | (35.0000) | Solvent |
| Total | 92.5 | 123.0 | 245.0 | |

Added as tesofensine citrate, and corresponds to a dose strength of 0.25 mg, 0.5 mg or 1.0 mg, respectively, of tesofensine free base. //
*Volatile components.

EXAMPLE 4

Composition D

Tesofensine coated tablets with a dose strength of 0.5 mg were developed based on the selection of pharmaceutically acceptable excipients. The qualitative and quantitative formulation of the coated tablet is shown in table 4.

The preparation method was similar to the method used for of compositions A, B, and C.

TABLE 4

Qualitative and quantitative composition of tesofensine coated tablets. Composition D.

| Ingredient | Composition 0.5 mg mg/tablet Tablet diameter 6 mm | Function |
|---|---|---|
| Tablet core | | |
| Tesofensine# | 0.3963 | Active |
| Lactose monohydrate | 59.004 | Filler |
| Microcrystalline cellulose | 56.100 | Filler/Binder |
| Hydroxypropylcellulose | 0.9000 | Binder |
| Croscarmellose sodium | 2.400 | Disintegrant |
| Magnesium stearate | 1.200 | Lubricant |
| Film coat | | |
| Opadry BROWN 03F23992 | 3.000 | Film coat |
| Total | 123.000 | |

Dissolution Profile

Figure 2:
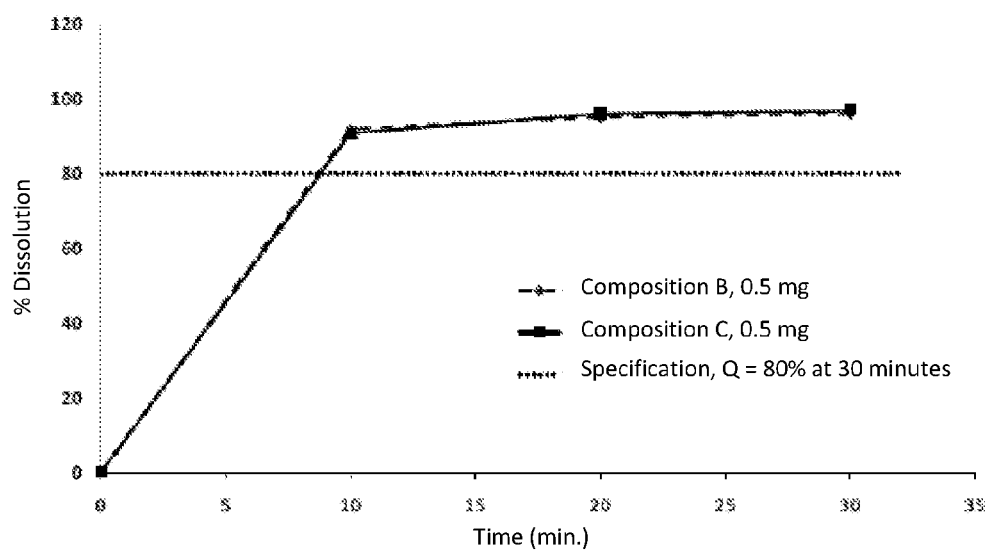
FIG. 2 is a chart showing the dissolution profile of two pharmaceutical compositions of tesofensine formulated as coated tablets with a dose-strength of 0.5 mg.
Figure 3:
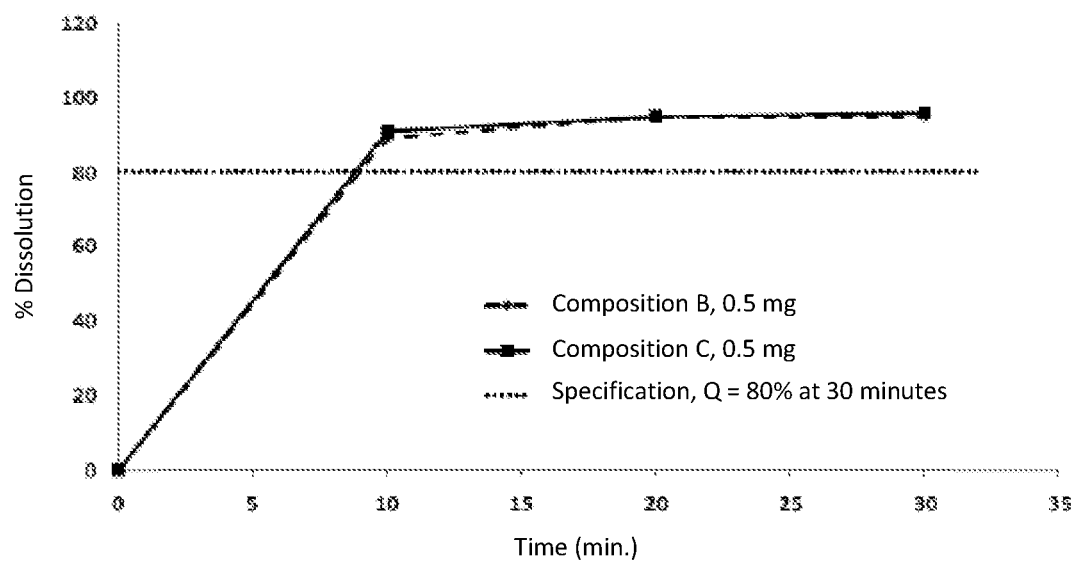
FIG. 3 is a chart showing the dissolution profile of two pharmaceutical compositions of tesofensine formulated as coated tablets with a dose-strength of 1.0 mg.

Dissolution tests indicated that tesofensine is a highly permeable and readily soluble compound. The active ingredient dissolves from the coated tablets within 30 minutes. FIGS. 1, 2 and 3 show dissolution profiles for tesofensine compositions B and C with a dose strength of 0.25 mg, 0.5 mg and 1.0 mg.

Stability Tests

Compositions of the tesofensine coated tablets of examples 1, 2 and 3 with a dose strength of 0.25 mg, 0.5 mg and 1.0 mg were evaluated to determine the stability of the same. The following parameters were measured during the stability test: appearance (Table 5), dissolution rate (Table 6), tesofensine degradation measured using HPLC (Table 7), tesofensine assay measured using HPLC (Table 8) and compression strength (Table 9). The stability of the coated tablets stored in PVC/PVCD-aluminum blisters and HDPE bottles was evaluated.

The stability studies of coated tablets stored in PVC/PVDC-aluminum blisters demonstrated that the appearance of the coated tablets did not change during the testing period (Table 5). Likewise, no significant changes were observed for the testing parameters: dissolution rate (Table 6), tesofensine degradation (Table 7), tesofensine assay (Table 8) and compression strength (Table 9). A tendency to decrease was observed for the compression strength, especially at the accelerated and intermediate condition for all dose strengths and all compositions, without it being a significant change.

The coated tablets showed tendency of chemical degradation when stored in PVC/PVDC-blisters. Two degradation products were identified during storage for all storage conditions. However, degradation products were below the identification and qualification thresholds. All tested parameters were within the corresponding specifications for all compositions, all dose strengths and all storage conditions.

The stability studies for coated tablets stored in HDPE bottles demonstrated that the appearance of the coated tablets did not change during the testing period (Table 5). Likewise, no significant changes were observed for the testing parameters: dissolution rate (Table 6), tesofensine degradation (Table 7), tesofensine assay (Table 8) and compression strength (Table 9). A tendency to decrease was observed for the compression strength, especially at the accelerated and intermediate condition for all dose strengths, without it being a significant change.

Two degradation products were identified during storage for all storage conditions. However, degradation products were below the identification and qualification thresholds. All tested parameters were within the corresponding specifications for all compositions, all dose strengths and all storage conditions.

In another stability test, the coated tablets were stored in open containers for 22 hours under light (Xenon lamp, ca. 1.2 million lux-hours) at room temperature and humidity. The coated tablets did not show any evidence of chemical degradation after storage in open containers when exposed to light.

Based on these findings, the inventors determined that the drug product does not require any special storage conditions.

The stability studies confirm that the tesofensine coated tablets are chemically stable. In addition, the stability studies justify that the coated tablets can be stored in PVC/PVDC-blisters or HDPE-bottles below 30° C. for up to 36 months in PVC/PVDC-blisters and for up to 24 months in HDPE-bottles.

TABLE 5

Stability results. Appearance.

Composition A-PVC/PVDC-blister
Specification: salmon coloured, round biconvex, film-coated tablets.

| Dose strength (mg) | Initial | Month 12 | | Month 24 | | Month 40 | |
|---|---|---|---|---|---|---|---|
| | | 25° C./60% HR | 30° C./70% HR | 25° C./60% HR | 30° C./70% HR | 25° C./60% HR | 30° C./65% HR |
| 0.25 | 1 | 1 | 1 | 1 | 1 | 1 | 1 |
| 0.5 | 1 | 1 | 1 | 1 | 1 | 1 | 1 |
| 1.0 | 1 | 1 | 1 | 1 | 1 | 1 | 1 |

Composition A-30 mL HDPE
Specification: salmon coloured, round biconvex, film-coated tablets.

| Dose strength (mg) | Initial | Month 12 | | Month 40 | | Month 60 | |
|---|---|---|---|---|---|---|---|
| | | 25° C./60% HR | 30° C./70% HR | 25° C./60% HR | 30° C./65% HR | 25° C./60% HR | 30° C./65% HR |
| 0.25 | 1 | 1 | 1 | 1 | 1 | 1 | 1 |
| 0.5 | 1 | 1 | 1 | 1 | 1 | 1 | 1 |
| 1.0 | 1 | 1 | 1 | 1 | 1 | 1 | 1 |

Composition B-PVC/PVDC-blister
Specification: salmon coloured, round biconvex, film-coated tablets.

| Dose strength (mg) | Initial | Month 12 | | Month 24 | | Month 36 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 1 | 1 | 1 | 1 | 1 | 1 | 1 |
| 0.5 | 1 | 1 | 1 | 1 | 1 | 1 | 1 |
| 1.0 | 1 | 1 | 1 | 1 | 1 | 1 | 1 |

TABLE 5-continued

Stability results. Appearance.

Composition B-30 mL HDPE
Specification: salmon coloured,
round biconvex, film-coated tablets.

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.5 | 1 | 1 | 1 | 1 | 1 | 1 | 1 |
| 1.0 | 1 | 1 | 1 | 1* | — | 1 | 1 |

Composition C-PVC/PVDC-blister
Specification: red-brown coloured,
round biconvex, film-coated tablets.

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 1 | 1 | 1 | 1 | — | 1 | 1 |
| 0.5 | 1 | 1 | 1 | 1 | — | 1 | 1 |
| 1.0 | 1 | 1 | 1 | 1 | — | 1 | 1 |

Composition C-30 mL HDPE
Specification: red-brown coloured,
round biconvex, film-coated tablets.

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 1 | 1 | 1 | 1 | — | 1 | 1 |
| 0.5 | 1 | 1 | 1 | 1 | — | 1 | 1 |
| 1.0 | 1 | 1 | 1 | 1 | — | 1 | 1 |

1 = Meets specification.
*Stability at month 20.

TABLE 6

Stability results. Dissolution test (Q), results
expressed as average dissolution rate (%).

Composition A-PVC/PVDC-blister
Specification: Q = 80 (30 min)

| Dose strength (mg) | Intial | Month 12 | | Month 24 | | Month 40 | |
|---|---|---|---|---|---|---|---|
| | | 25° C./60% HR | 30° C./70% HR | 25° C./60% HR | 30° C./70% HR | 25° C./60% HR | 30° C./65% HR |
| 0.25 | 99 | 98 | 95 | 95 | 94 | 99 | 98 |
| 0.5 | 97 | 99 | 98 | 97 | 95 | 100 | 98 |
| 1.0 | 97 | 98 | 97 | 96 | 96 | 96 | 97 |

Composition A-30 mL HDPE
Specification Q = 80 (30 min)

| Dose strength (mg) | Intial | Month 12 | | Month 40 | | Month 60 | |
|---|---|---|---|---|---|---|---|
| | | 25° C./60% HR | 30° C./70% HR | 25° C./60% HR | 30° C./65% HR | 25° C./60% HR | 30° C./65% HR |
| 0.25 | 99 | 98 | 96 | 98 | 97 | 98 | 97 |
| 0.5 | 97 | 100 | 97 | 98 | 96 | 99 | 99 |
| 1.0 | 97 | 99 | 97 | 99 | 98 | 99 | 99 |

TABLE 6-continued

Stability results. Dissolution test (Q), results
expressed as average dissolution rate (%).

Composition B-PVC/PVDC-blister
Specification: Q = 80 (30 min)

| Dose strength (mg) | Intial | Month 12 | | Month 24 | | Month 36 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 97 | 101 | 102 | 99 | 98 | 98 | 99 |
| 0.5 | 98 | 102 | 101 | 98 | 98 | 98 | 96 |
| 1.0 | 97 | 100 | 101 | 98 | 96 | 98 | 98 |

Composition B-30 mL HDPE
Specification: Q = 80 (30 min)

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.5 | 100 | 102 | 99 | 100 | 102 | 99 | 99 |
| 1.0 | 96 | 96 | 97 | 98* | — | 98 | 98 |

Composition C-PVC/PVDC-blister
Specification: Q = 80 (30 min)

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 99 | 102 | 100 | 101 | — | 100 | 102 |
| 0.5 | 97 | 103 | 97 | 101 | — | 101 | 99 |
| 1.0 | 96 | 99 | 98 | 98 | — | 99 | 100 |

Composition C-30 mL HDPE
Specification: Q = 80 (30 min)

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 99 | 98 | 100 | 100 | — | 98 | 100 |
| 0.5 | 97 | 104 | 101 | 99 | — | 100 | 100 |
| 1.0 | 96 | 98 | 98 | 102 | — | 100 | 99 |

*Stability at month 20.

TABLE 7

Stability results. Degradation of tesofensine, expressed as % w/w.

Composition A-PVC/PVDC-Blister
Specification: ≤2.0.

| Dose strength (mg) | Intial | Month 12 | | Month 24 | | Month 40 | |
|---|---|---|---|---|---|---|---|
| | | 25° C./60% HR | 30° C./70% HR | 25° C./60% HR | 30° C./70% HR | 25° C./60% HR | 30° C./65% HR |
| 0.25 | 0.2 | 0.3 | 0.3 | 0.2 | 0.7 | 0.7 | 1.2 |
| 0.5 | 0.2 | 0.2 | 0.3 | 0.2 | 0.3 | 0.5 | 0.9 |
| 1.0 | 0.2 | 0.2 | 0.3 | 0.2 | 0.3 | 0.3 | 0.8 |

TABLE 7-continued

Stability results. Degradation of tesofensine, expressed as % w/w.

Composition A-30 mL HDPE
Specification: ≤2.0

| Dose strength (mg) | Intial | Month 12 | | Month 40 | | Month 60 | |
|---|---|---|---|---|---|---|---|
| | | 25° C./60% HR | 30° C./70% HR | 25° C./60% HR | 30° C./65% HR | 25° C./60% HR | 30° C./65% HR |
| 0.25 | 0.2 | 0.2 | 0.2 | 0.3 | 0.8 | 0.4 | 1.0 |
| 0.5 | 0.2 | 0.2 | 0.2 | 0.3 | 0.4 | 0.4 | 0.6 |
| 1.0 | 0.2 | 0.2 | 0.2 | 0.3 | 0.4 | 0.2 | 0.3 |

Composition B-PVC/PVDC-blister
Specification: ≤2.0

| Dose strength (mg) | Intial | Month 12 | | Month 24 | | Month 36 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | <0.1 | <0.1 | <0.1 | <0.1 | <0.1 | <0.1 | 0.36 |
| 0.5 | <0.1 | <0.1 | <0.1 | <0.1 | <0.1 | <0.1 | 0.39 |
| 1.0 | <0.1 | <0.1 | <0.1 | <0.1 | <0.1 | <0.1 | 0.31 |

Composition B-30 mL HDPE
Specification: ≤2.0

| Dose Strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.5 | <0.18 | <0.1 | <0.1 | <0.1 | <0.1 | <0.1 | <0.1 |
| 1.0 | <0.1 | <0.1 | <0.1 | <0.1* | — | <0.1 | <0.1 |

Composition C-PVC/PVDC-blister
Specification: ≤2.0

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | <0.10 | <0.10 | <0.11 | <0.10 | — | 0.10 | 0.14 |
| 0.5 | <0.10 | <0.10 | <0.10 | <0.10 | — | <0.10 | 0.13 |
| 1.0 | — | <0.10 | <0.10 | <0.10 | — | <0.10 | 0.12 |

Composition C-30 mL HDPE
Specification: ≤2.0

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | — | <0.10 | <0.10 | <0.10 | — | <0.10 | <0.10 |
| 0.5 | — | <0.10 | <0.10 | <0.10 | — | <0.10 | <0.10 |
| 1.0 | — | <0.10 | <0.10 | <0.10 | — | <0.10 | <0.10 |

*Stability at month 20.

TABLE 8

Stability results. Tesofensine assay, expressed as mg/tablet.

Composition A-PVC/PVDC-blister
Specification: 0.233-0.262 for 0.25 mg;
0.465-0.525 for 0.5 mg,
0.930-1.050 for 1.0 mg.

| Dose strength (mg) | Intial | Month 12 | | Month 24 | | Month 40 | |
|---|---|---|---|---|---|---|---|
| | | 25° C./60% HR | 30° C./70% HR | 25° C./60% HR | 30° C./70% HR | 25° C./60% HR | 30° C./65% HR |
| 0.25 | 0.248 | 0.247 | 0.249 | 0.245 | 0.243 | 0.243 | 0.243 |
| 0.5 | 0.498 | 0.503 | 0.497 | 0.491 | 0.492 | 0.491 | 0.483 |
| 1.0 | 1.007 | 1.005 | 1.014 | 0.984 | 0.988 | 0.981 | 0.955 |

Composition A-30 mL HDPE
Specification: 0.233-0.262 for 0.25 mg;
0.465-0.525 for 0.5 mg,
0.930-1.050 for 1.0 mg.

| Dose strength (mg) | Intial | Month 12 | | Month 40 | | Month 60 | |
|---|---|---|---|---|---|---|---|
| | | 25° C./60% HR | 30° C./70% HR | 25° C./60% HR | 30° C./65% HR | 25° C./60% HR | 30° C./65% HR |
| 0.25 | 0.248 | 0.249 | 0.249 | 0.243 | 0.242 | 0.245 | 0.246 |
| 0.5 | 0.491 | 0.504 | 0.503 | 0.492 | 0.488 | 0.494 | 0.495 |
| 1.0 | 1.007 | 1.009 | 1.004 | 0.979 | 0.981 | 0.996 | 0.993 |

TABLE 8-continued

Stability results. Tesofensine assay, expressed as mg/tablet.

Composition B-PVC/PVDC-blister
Specification: 0.233-0.262 for 0.25 mg;
0.465-0.525 for 0.5 mg,
0.930-1.050 for 1.0 mg.

| Dose strength (mg) | Intial | Month 12 | | Month 24 | | Month 36 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 0.247 | 0.243 | 0.246 | 0.248 | 0.244 | 0.248 | 0.244 |
| 0.5 | 0.492 | 0.496 | 0.492 | 0.502 | 0.495 | 0.498 | 0.491 |
| 1.0 | 0.970 | 0.980 | 0.977 | 0.978 | 0.981 | 0.986 | 0.983 |

Composition B-30 mL HDPE
Specification: 0.465-0.525 for 0.5 mg,
0.930-1.050 for 1.0 mg.

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.5 | 0.494 | 0.495 | 0.498 | 0.501 | 0.499 | 0.498 | 0.498 |
| 1.0 | 0.972 | 0.982 | 0.983 | 0.979* | — | 0.990 | 0.980 |

Composition C-PVC/PVDC-blister
Specification: 0.238-0.262 for 0.25 mg,
0.475-0.525 for 0.5 mg,
0.95-1.05 for 1.0 mg.

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 0.245 | 0.244 | 0.243 | 0.247 | — | 0.251 | 0.252 |
| 0.5 | 0.492 | 0.488 | 0.491 | 0.487 | — | 0.495 | 0.490 |
| 1.0 | 0.99 | 0.98 | 0.99 | 0.98 | — | 0.99 | 1.00 |

Composition C-30 mL HDPE
Specification: 0.238-0.262 for 0.25 mg,
0.475-0.525 for 0.5 mg,
0.95-1.05 for 1.0 mg.

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 0.245 | 0.245 | 0.247 | 0.249 | — | 0.251 | 0.251 |
| 0.5 | 0.492 | 0.492 | 0.494 | 0.490 | — | 0.501 | 0.497 |
| 1.0 | 0.99 | 0.97 | 0.98 | 0.98 | — | 0.99 | 0.99 |

*Stability at month 20.

TABLE 9

Stability results. Compression strength/Resistance to crushing (N), expressed as the average compression strength.

Composition A-PVC/PVDC-blister
Specification: 20-110 for 0.5 mg, 20-130 for 0.5 mg, 20-160 for 1.0 mg.

| Dose strength (mg) | Intial | Month 12 | | Month 24 | | Month 40 | |
|---|---|---|---|---|---|---|---|
| | | 25° C./60% HR | 30° C./70% HR | 25° C./60% HR | 30° C./70% HR | 25° C./60% HR | 30° C./65% HR |
| 0.25 | 70 | 63 | 56 | 61 | 56 | 61 | 53 |
| 0.5 | 67 | 59 | 55 | 59 | 57 | 58 | 52 |
| 1.0 | 94 | 83 | 71 | 86 | 72 | 76 | 71 |

Composition A-30 mL HDPE
Specification: 20-110 for 0.5 mg, 20-130 for 0.5 mg, 20-160 for 1.0 mg.

| Dose strength (mg) | Intial | Month 12 | | Month 40 | | Month 60 | |
|---|---|---|---|---|---|---|---|
| | | 25° C./60% HR | 30° C./70% HR | 25° C./60% HR | 30° C./65% HR | 25° C./60% HR | 30° C./65% HR |
| 0.25 | 70 | 65 | 61 | 58 | 53 | 58 | 53 |
| 0.5 | 67 | 68 | 62 | 57 | 52 | 56 | 55 |
| 1.0 | 94 | 100 | 90 | 77 | 71 | 81 | 65 |

Composition B-PVC/PVDC-blister
Specification: 20-110 for 0.5 mg, 20-130 for 0.5 mg, 20-160 for 1.0 mg.

| Dose strength (mg) | Intial | Month 12 | | Month 24 | | Month 36 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 58 | 44 | 32 | 41 | 35 | 40 | 30 |
| 0.5 | 79 | 57 | 43 | 67 | 47 | 55 | 43 |
| 1.0 | 98 | 68 | 47 | 63 | 52 | 62 | 47 |

Composition B-30 mL HDPE
Specification: 20-130 for 0.5 mg, 20-160 for 1.0 mg.

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.5 | 87 | 75 | 69 | 71 | 62 | 67 | 58 |
| 1.0 | 111 | 97 | 93 | 97* | — | 91 | 86 |

Composition C-PVC/PVDC-blister
Specification: 20-110 for 0.5 mg, 20-130 for 0.5 mg, 20-160 for 1.0 mg.

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 63 | 46 | 38 | 40 | — | 51 | 44 |
| 0.5 | 84 | 60 | 44 | 53 | — | 62 | 49 |
| 1.0 | 117 | 87 | 69 | 76 | — | 93 | 66 |

Composition C-30 mL HDPE
Specification: 20-110 for 0.5 mg, 20-130 for 0.5 mg, 20-160 for 1.0 mg.

| Dose strength (mg) | Intial | Month 12 | | Month 18 | | Month 24 | |
|---|---|---|---|---|---|---|---|
| | | 25° C./60% HR | 30° C./65% HR | 25° C./60% HR | 30° C./65% HR | 25° C./60% HR | 30° C./65% HR |
| 0.25 | 63 | 51 | 50 | 56 | — | 51 | 46 |
| 0.5 | 84 | 78 | 65 | 66 | — | 70 | 58 |
| 1.0 | 117 | 110 | 101 | 105 | — | 104 | 95 |

*Stability at month 20.

The invention claimed is:

1. A stable, oral pharmaceutical composition comprising a coated tablet comprising:
   a) a tablet core consisting of
      90-98 weight % lactose monohydrate and microcrystalline cellulose;
      1-3 weight % crosscarmellose sodium;
      0.5-1.5 weight % magnesium stearate;
      0.5-1.5 weight % hydroxypropylcellulose; and
      tesofensine, or a pharmaceutically acceptable salt thereof; and
   b) a coating film;
   and
   wherein the sole active pharmaceutical ingredient in the composition is the tesofensine, or the pharmaceutically acceptable salt thereof.

2. The pharmaceutical composition according to claim 1, wherein the pharmaceutically acceptable excipients constitute from 96% to 98% by weight of the total weight of the composition, and the coating film constitutes from 2% to 3% by weight of the total weight of the composition.

3. The pharmaceutical composition according to claim 1, wherein the tablet core consists of:
   a) 40-80 weight % lactose monohydrate;
   b) 20-50 weight % microcrystalline cellulose;
   c) 1-3 weight % crosscarmellose sodium;
   d) 0.5-1.5 weight % magnesium stearate;
   e) 0.5-1.5 weight % hydroxypropylcellulose; and
   f) tesofensine, or a pharmaceutically acceptable salt thereof.

4. The pharmaceutical composition according to claim 1, wherein the coating film comprises one or more components selected from the group consisting of coating agents, plasticizers, solvents, glidants, and pigments.

5. The pharmaceutical composition according to claim 4, wherein the coating agent is hypromellose.

6. The pharmaceutical composition according to claim 4, wherein the plasticizer is macrogol.

7. The pharmaceutical composition according to claim 4, wherein the glidant is talcum.

8. The pharmaceutical composition according to claim 4, wherein the pigment is selected from the group consisting of titanium oxide and iron oxide.

9. The pharmaceutical composition according to claim 4, wherein the solvent is selected from the group consisting of water and ethanol.

10. The pharmaceutical composition according to claim 4, wherein the coating film comprises:
   a. 30-70 weight % coating agent;
   b. 2.5-10 weight % plasticizer;

c. 20-40 weight % pigment; and
d. 10-20% glidant.

11. The pharmaceutical composition according to claim 4, wherein the coating film comprises:
   a. 30-70 weight % hypromellose;
   b. 2.5-10 weight % macrogol 6,000;
   c. 20-30 weight % titanium oxide;
   d. 2.5-7.5 weight % iron oxide; and
   e. 10-20% talcum.

12. The pharmaceutical composition according to claim 1, wherein the coating film comprises hypromellose, titanium dioxide, macrogol 6,000, talcum, and iron oxide.

13. A stable, oral pharmaceutical composition comprising a coated tablet comprising:
   a) a tablet core comprising tesofensine, or a pharmaceutically acceptable salt thereof, intimately mixed with pharmaceutically acceptable excipients selected from the group consisting of hydroxypropylcellulose, lactose monohydrate, croscarmellose sodium, microcrystalline cellulose, magnesium stearate, and combinations thereof, and optionally a solvent and
   b) a coating film;
wherein the sole active pharmaceutical ingredient in the composition is the tesofensine, or the pharmaceutically acceptable salt thereof; and
wherein the tablet core does not comprise povidone (polyvinylpyrrolidone, PVP), crospovidone (polyvinylpolypyrrolidone, PVPP), copovidone (polyvinylpyrrolidone vinylacetate copolymer), macrogol (polyethyleneglycol, PEG), or titanium dioxide.

14. The pharmaceutical composition according to claim 1, wherein the pharmaceutically acceptable salt of tesofensine is tesofensine citrate.

15. A process to prepare the composition according to claim 1, comprising the steps of:
   a) forming a tablet core consisting of
      90-98 weight % lactose monohydrate and microcrystalline cellulose;
      1-3 weight % crosscarmellose sodium;
      0.5-1.5 weight % magnesium stearate;
      0.5-1.5 weight % hydroxypropylcellulose; and
      tesofensine, or a pharmaceutically acceptable salt thereof; and
   b) forming the coated tablet by spraying the coating film onto the tablet core, wherein the coating film constitutes from 2% to 3% by weight of the total weight of the composition.

16. The method of claim 15, wherein the tablet core is prepared by:
   a) dissolving tesofensine, or a pharmaceutically acceptable salt thereof, and hydroxypropylcellulose in a granulation liquid to obtain a granulation liquid mixture;
   b) wetting lactose monohydrate with the granulation liquid mixture to form a wetted granulate;
   c) drying and sieving the wetted granulate;
   d) mixing the wetted granulate with croscarmellose sodium, microcrystalline cellulose, and magnesium stearate to form a final blend; and
   e) tableting the final blend into tablet cores.

17. The pharmaceutical composition of claim 1, wherein the tablet core consists of
   90-98 weight % lactose monohydrate and microcrystalline cellulose;
   1-3 weight % crosscarmellose sodium;
   0.5-1.5 weight % magnesium stearate;
   0.5-1.5 weight % hydroxypropylcellulose; and
   0.25 mg to 1 mg of tesofensine, measured as the free base.

18. The pharmaceutical composition of claim 1, wherein the tablet core consists of
   90-98 weight % lactose monohydrate and microcrystalline cellulose;
   1-3 weight % crosscarmellose sodium;
   0.5-1.5 weight % magnesium stearate;
   0.5-1.5 weight % hydroxypropylcellulose; and
   0.25 mg of tesofensine, measured as the free base.

19. The pharmaceutical composition of claim 1, wherein the tablet core consists of
   90-98 weight % lactose monohydrate and microcrystalline cellulose;
   1-3 weight % crosscarmellose sodium;
   0.5-1.5 weight % magnesium stearate;
   0.5-1.5 weight % hydroxypropylcellulose; and
   0.5 mg of tesofensine, measured as the free base.

20. The pharmaceutical composition of claim 1, wherein the tablet core consists of
   90-98 weight % lactose monohydrate and microcrystalline cellulose;
   1-3 weight % crosscarmellose sodium;
   0.5-1.5 weight % magnesium stearate;
   0.5-1.5 weight % hydroxypropylcellulose; and
   1 mg of tesofensine, measured as the free base.

21. The pharmaceutical composition of claim 1, wherein the tablet core consists of
   90-98 weight % lactose monohydrate and microcrystalline cellulose;
   1-3 weight % crosscarmellose sodium;
   0.5-1.5 weight % magnesium stearate;
   0.5-1.5 weight % hydroxypropylcellulose; and
   0.2-0.7 weight % tesofensine, measured as the free base.

22. The pharmaceutical composition of claim 13, wherein the tablet core further does not comprise colloidal silicon dioxide.

23. The pharmaceutical composition of claim 13, wherein the tablet core comprises 0.25 mg to 1 mg of tesofensine, measured as the free base.

24. The pharmaceutical composition of claim 13, wherein the tablet core comprises 0.25 mg of tesofensine, measured as the free base.

25. The pharmaceutical composition of claim 13, wherein the tablet core comprises 0.5 mg of tesofensine, measured as the free base.

26. The pharmaceutical composition of claim 13, wherein the tablet core comprises 1 mg of tesofensine, measured as the free base.

27. The pharmaceutical composition of claim 13, wherein the tablet core comprises 0.2-0.7 weight % tesofensine, measured as the free base.

* * * * *